US00PP08205P

United States Patent [19]

Nelson et al.

[11] Patent Number: Plant 8,205

[45] Date of Patent: Apr. 20, 1993

[54] STRAWBERRY PLANT NAMED 'PSI-.118'

[75] Inventors: Steven D. Nelson; Michael D. Nelson, both of Watsonville; Daniel T. Schmida, Aptos, all of Calif.

[73] Assignee: Plant Sciences, Inc., Watsonville, Calif.

[21] Appl. No.: 635,220

[22] Filed: Dec. 27, 1990

[51] Int. Cl.[5] ..... A01H 5/00

[52] U.S. Cl. ..... Plt./49

[58] Field of Search ..... Plt. 48, 49

[56] References Cited

U.S. PATENT DOCUMENTS

P.P. 4,487 11/1979 Bringhurst et al. ..... Plt. 49
P.P. 4,538 5/1980 Bringhurst et al. ..... Plt. 49
P.P. 5,262 7/1984 Voth et al. ..... Plt. 48
P.P. 5,266 7/1984 Bringhurst et al. ..... Plt. 49
P.P. 6,558 1/1989 Bringhurst et al. ..... Plt. 49
P.P. 7,172 2/1990 Voth et al. ..... Plt. 49

*Primary Examiner*—James R. Feyrer
*Attorney, Agent, or Firm*—Foley & Lardner

[57] ABSTRACT

This invention relates to a new distinct short day type strawberry variety named 'PSI-.118'. The new variety produces a relatively high fruit yield, greater than 'Muir', but less than 'Selva'. The variety is characterized by its medium to large, smooth and conic, relatively dark colored fruit having excellent flavor, better than 'Selva' and 'Muir', and excellent firmness, resulting in shipping quality comparable to, or better than, the standard cultivars. The variety is also distinguished by its dark foliage, slightly downwardly cupped at the tips, and its erect growth habit.

4 Drawing Sheets

INTRODUCTION

This invention relates to a new and distinct short day type strawberry variety designated 'PSI-.118' (hereafter '118'). The variety is botanically identified as *F. chiloensis* Duch. var. *ananasa*. The new variety results from a breeding program initiated jointly by Plant Sciences, Inc. and Coast Cooling, Inc., both of Watsonville, Calif., with the goal of developing new and distinct strawberry varieties.

Variety '118' was discovered as a chance seedling in a breeding plot established in November, 1987, on a ranch in Watsonville, Calif., provided by Well-Pict, Inc. The seedling had been grown and asexually propagated by stolons during the spring and summer of 1987 in a seedling nursery located in Lassen County, Calif. After being selected in the spring of 1988, clones of the new variety, which had been produced in 1987, were further asexually propagated in the nursery and extensively tested the following fruiting season (1988–89). This propagation demonstrated that the combination of characteristics disclosed herein for the new variety are fixed and retained through successive generations of asexual reproduction.

The following characteristics are particularly distinguishing and outstanding in '118':

1. Short day type fruiting habit.
2. Medium to large, dark colored fruit having excellent flavor, juiciness and gloss.
3. Excellent post harvest fruit holding quality.
4. Fruit borne on erect peduncles and pedicels, exposed and relatively easy to harvest.
5. Erect, vigorous plant when given proper chilling, dark colored. Capable of producing fresh market fruit from April through October.

DESCRIPTION OF THE PHOTOGRAPHIC DRAWINGS

The accompanying photographs, taken in both greenhouse filtered and outdoor field sunlight in Watsonville, Calif., show typical specimens of '118' at various stages of development.

Sheet 1 shows typical early season plant parts of the new variety, including leaves, individual flowers, inflorescences and mature fruit. The underside of a mature leaflet plus the upper surface of a trifoliate leaf are pictured, both showing typical moderately deep serrations. Two inflorescences are shown, one with all immature fruit, and the other with the primary fruit being mature and harvestable. Also shown are cross-sectional and longitudinal views of mature fruit, illustrating typical flesh coloring, and a conspicuous core and core cavity.

Sheet 2 shows typical plant growth, flowering and fruiting characteristics in mid-June. The photograph illustrates how fruit are borne on relatively erect peduncles and pedicels, which extend beyond the foliage, thus exposing the fruit for easy harvesting. Also shown are the relatively dark leaves, slightly downwardly cupped at the leaf margins.

Sheet 3 is a close-up view of fruit harvested on Jun. 27, 1990 and packed in a standard twelve dry pint crate. As seen, few fruit become seedy at the apex during this time of the season. Earlier in the season, a greater percentage of fruit have seedy tips.

The FIGURE discloses isozyme banding patterns for the variety PSI-118, compared with those for Selva.

FRUIT PRODUCTION CHARACTERISTICS

Variety '118' is primarily adapted to the climate and growing conditions of the central coast of California, where it was selected. This region provides the necessary cold winter temperatures required for it to produce a strong vigorous plant and remain in fruit production from April through October. The nearby Pacific ocean provides humidity and cool temperatures needed to maintain fruit quality during the summer production months. Variety '118' has a lower vernalization (chilling) requirement than 'Selva' (U.S. Plant Pat. No. 5,266), and is less sensitive to excessive or reduced winter chilling experienced in the fruiting bed.

Winter planted '118' begins fruiting mid to late April, about two to three weeks later than the day neutral cultivars 'Selva' and 'Muir' (U.S. Plant Pat. No. 6,558). Initial yield studies have shown that '118' is capable of producing a total marketable fruit yield which falls between the two winter planted commercial standard cultivars, 'Muir' and 'Selva', being greater than 'Muir' but less than 'Selva', with a season average fruit size almost as large as each of the two standard cultivars (Table 1).

TABLE 1

1989 marketable fruit yield and size comparison of high elevation (Susanville, California) '118' plants with standard cultivars dug October 20, 1988 and planted November 11, 1988 in Watsonville, California.

| | MONTHLY YIELDS - GRAMS/PLANT | | | | |
|---|---|---|---|---|---|
| CULTIVAR | 4/30 | 5/31 | 6/30 | 7/31 | 8/31 |
| '118' | 10 | 46 | 108 | 228 | 238 |
| 'SELVA' | 78 | 143 | 66 | 321 | 218 |
| 'MUIR' | 19 | 84 | 96 | 203 | 161 |

| | MONTHY YIELDS - GRAMS/PLANT | | TOTAL | SIZE |
|---|---|---|---|---|
| CULTIVAR | 9/30 | 10/31 | G/PL | G/FR |
| '118' | 121 | 30 | 781 | 19.3 |
| 'SELVA' | 113 | 39 | 978 | 20.2 |
| 'MUIR' | 109 | 20 | 692 | 20.1 |

VARIETAL DESCRIPTION

Following is a detailed description of the new variety based on observations taken in July and August, 1990 from plants that were planted in November, 1989 in Watsonville, Calif. Color terminology is in accordance with the Munsell Book of Colors, Munsell Color, Baltimore, Md. (1976).

Parentage: '118' is the result of an open pollinated seedling of unknown parentage.

FRUIT

Fruit shape is characteristically medium conic, with some fruit having wedged tips. Fan or wedge shaped fruit having longitudinal grooves occur less frequently than in 'Selva' and 'Muir'. Fruit are relatively broad, ovate in outline, having smooth rounded shoulders which extend slightly above the point where the calyx attaches to the berry. Achenes are bright yellow, but will turn dark red upon prolonged exposure to sunlight. The achenes are typically positioned exerted from the berry surface, with few flush and are spaced evenly over the entire fruit surface except during the early season (May–June) when the fruit apexes become seedy. This tends to cause the tips to remain "green" even when fruit are ripe and ready for harvest. Fruit are more juicy and more glossy than 'Selva' and 'Muir', with a noticeable aroma and excellent flavor, better than that of the standard cultivars. The primary fruit typically have a conspicuous core and hollow core cavity. Secondary and tertiary fruit may or may not have a hollow core cavity. Fruit quality characteristics including color, soluble solids, firmness and calyx diameter are compared with those of 'Selva' and 'Muir' in Table 2.

TABLE 2

Comparison of mid-summer 1990 fruit quality characteristics of '118', 'Selva' and 'Muir' from fruit produced in Watsonville, California

| | SURFACE COLOR | % SOLUBLE SOLIDS | |
|---|---|---|---|
| CULTIVAR | (MUNSELL) | RANGE | AVERAGE |
| '118' | 7.5R 3/10 to 7.5R 2/8 | 6.5–8.0 | 6.9 |
| 'SELVA' | 7R 4/11* | 7.2–7.8 | 7.4 |
| 'MUIR' | 7R 4.5/13* | 7.5–8.3 | 7.8 |

| | FIRMNESS RATING | CALYX DIAMETER (MM) | |
|---|---|---|---|
| CULTIVAR | (0–10) | RANGE | AVERAGE |
| '118' | 8.6 | 33–54 | 43 |
| 'SELVA' | 8.8 | 26–42 | 34 |
| 'MUIR' | 8.1 | 23–41 | 32 |

*'Selva' and 'Muir' fruit surface color according to Voth et al., United States Plant Patent No. 7,172 ('Irvine') 1990.

The skin surface and flesh are considered dark, darker than both 'Selva' and 'Muir'. Refractometer readings indicate that the fruit have a slightly lower percentage of soluble solids than 'Selva' or 'Muir'. Fruit are nearly as firm as 'Selva' and slightly firmer than 'Muir', and store and ship as well or slightly better than both standard cultivars. Calyx diameter is medium to large, considerably larger than that of 'Selva' and 'Muir'. The calyx consists of an average of 12 to 16 sepals, and attaches firmly to slightly below the base of the fruit, rarely on a neck. The sepals are narrow ovate in shape, having acute apexes and few serrations, with some overlapping.

PLANT

Variety '118' is capable of producing a strong vigorous plant when given the proper chilling, comparable to 'Selva' and stronger than 'Muir' and more densely foliated than the two standard cultivars. Excessive chilling will result in an over-vigorous plant and a reduction in total fruit yield. The crown branches similarly to 'Selva' and 'Muir', but does not attach to the soil as firmly as the two standard cultivars. Plants of '118' are considerably more erect than 'Selva', slightly more erect than 'Muir', but not quite as erect as 'Irvine' (U.S. Plant Pat. No. 7,172).

Foliage

Leaf characteristics are compared with those of 'Selva' and 'Muir' in Table 3.

TABLE 3

Comparison of mid-summer 1990 leaf characteristics of '118', 'Selva' and 'Muir' from plants grown in Watsonville, California

| CHARACTER | '118' | 'SELVA' | 'MUIR' |
|---|---|---|---|
| Munsell Leaf Color (Upper Surface) | 7.5 GY 3/4 | 7.5 GY 4/4 | 2.5 GY 4/3 |
| Petiole Length (CM) | 24.9 | 22.5 | 22.0 |
| Petiolule Length (MM) | 16.5 | 13.7 | 6.7 |
| Terminal Leaflet Size - L × W (CM) | 9.6 × 8.7 | 9.3 × 8.2 | 8.9 × 8.3 |
| Terminal Leaflet Ratio (L/W) | 1.10 | 1.13 | 1.07 |
| Terminal Leaflet Basal Angle (Degrees) | 53.1 | 50.4 | 63.2 |
| No. of Serrations (½ Terminal Leaflet) | 11.5 | 11.1 | 10.7 |

TABLE 3-continued

| Comparison of mid-summer 1990 leaf characteristics of '118', 'Selva' and 'Muir' from plants grown in Watsonville, California | | | |
|---|---|---|---|
| CHARACTER | '118' | 'SELVA' | 'MUIR' |
| Serration Depth (MM) | 5.8 | 4.7 | 5.6 |

Leaves are slightly darker than those of 'Selva' and 'Muir'. Petioles are slightly longer than those of 'Selva' and 'Muir'. Terminal leaflet petiolules are slightly longer than those of 'Selva', yet considerably longer than those of 'Muir'. Terminal leaflets are slightly larger than those of the standard cultivars, as shown by the length×width measurements. The shape of the terminal leaflet is described by the ratio of length/width and the basal angle, both of which indicate that '118' terminal leaflets are slightly more round than those of 'Selva', but less round than those of 'Muir'. Terminal leaflets have slightly more serrations per half terminal leaflet than 'Selva' and 'Muir'. These serrations are moderately deep, deeper than those of 'Selva', but comparable in depth to those of 'Muir', having moderately acute apexes with some overlapping. Bract leaflets occur in fewer than half of the petioles and may occur singly or in pairs. Pubescence on the petioles grow irregularly perpendicular to the petiole. Light pubescence is also present on the upper and lower leaf surfaces, irregularly parallel to these surfaces. Leaf surfaces are moderately rugose. Leaflets are slightly downwardly cupped at the margins.

Isozymes in Leaf Extract

Studies of protein polymorphism by the starch gel electrophoresis method were carried out to characterize this newly developed variety and further distinguish it from other varieties. The following isozymes were extracted from young leaves and characterized: phosphoglucoisomerase (PGI: EC 5.3, 1.9), phosphoglucomutase (PGM: EC 2.7.5.1) and leucine aminopeptidase (LAP: EC 3.4.11.1). The plant materials used were both field and greenhouse grown in Watsonville, Calif. Newly matured leaves (1 g fresh weight) were collected in the morning, held at 4°-8° C. and analyzed within 24 hours. Gel and electrode buffers for the enzyme systems analyzed are given in Table 4. Electrophoresis specifications for these enzyme systems are given in Table 5. The techniques and stains used are described in Arulsekar and Parfitt, "Procedures for Stone Fruits . . . " *Hort. Sci,* 21(4): 928-933.

TABLE 4

| Gel and electrode buffers for Fragaria enzyme systems | | | | | | |
|---|---|---|---|---|---|---|
| SYS- | | | | ELECTRODE | | |
| TEM | GEL BUFFER | G/L | pH | BUFFER | G/L | pH |
| A | TRIS BASE | 6.5 | 8.3 | LITHIUM HYDROXIDE | 1.2 | 8.3 |
| | CITRIC ACID (MONOHYD.) | 1.5 | | BORIC ACID | 12.0 | |
| B | DL-HISTIDINE HCL (MONOHYD.) | 1.2 | 7.0 | TRIS BASE | 16.5 | 7.0 |
| | | | | CITRIC ACID (MONOHYD.) | 9.0 | |

TABLE 5

| Fragaria electrophoresis specifications | | | | |
|---|---|---|---|---|
| SYSTEM | ENYZME | pH | CURRENT | GEL SLICE # |
| A | PGI | 8.3 | 275 V | 2 |
| A | LAP | 8.3 | 275 V | 4 |
| B | PGM | 7.0 | 150 V | 3 |

Following electrophoresis, the gel was sliced into three equal slices and stained for each enzyme system. Banding patterns were interpreted as they developed and gel slices were fixed in 50% glycerol. The RF value is the ratio between the distance (cm) traveled by the band to the distance traveled by the dye front (cm). The isozyme banding patterns for the three enzyme systems are compared to those of Selva in the Figure, and are compared to those of 'Selva', 'Muir', 'Irvine', 'Chandler', 'Pajaro' and 'Douglas' in Table 6. Variety '118' has a unique pattern which separates it from all University of California patented varieties based on a new pattern (A7) for PGI. This isozyme pattern differs from A4 in that the bottom band (RF.400) is very faint for A4, whereas RF.400 in A7 is moderately dark, similar to the density of bands at RF.434 and RF.472.

TABLE 6

| '118' Isozyme banding patterns compared to University of California patented cultivars | | | |
|---|---|---|---|
| CULTIVAR | PGI | LAP | PGM |
| '118' | A7 | B3 | C4 |
| 'SELVA' | A2 | B3 | C2 |
| 'MUIR' | A2 | B1 | C2 |
| 'IRVINE' | A3 | B1 | C2 |
| 'CHANDLER' | A1 | B3 | C1 |
| 'PAJARO' | A4 | B3 | C1 |
| 'DOUGLAS' | A3 | B3 | C1 |

INFLORESCENCE

Inflorescences are borne on relatively long, erect and thick primary peduncles, averaging about 25.0 cm long and 4.0 mm wide (July-August), which extend the inflorescences beyond the foliage during much of the season. Inflorescences are considerably longer and more erect than those of 'Selva', averaging 18.3 cm long, and 'Muir', averaging 15.0 cm long. At the apex of the primary peduncle originate two to four (most typically three) secondary peduncles and a pedicel bearing the primary berry. At times, pedicels bearing secondary and tertiary berries may originate singly from the apex of the primary peduncle rather than together in secondary peduncles. The pedicel bearing the primary berry may originate from the base of one of the secondary peduncles. Secondary and tertiary berries are borne on pedicels which are often longer than the pedicel bearing the primary berry.

Flowers are relatively large and produce ample pollen for good pollination except during the early season when seedy tipped fruit occur. Flowers are easily seen above the plant during certain periods of the season with an average of six obovate shaped petals per flower averaging 11.8 mm long and 11.1 mm wide. Typically, a bract leaflet ranging in shape from elliptical to ovate is borne on a short petiolule which originates at the primary peduncle apex alongside the base of one of the secondary peduncles. Sometimes, this bract leaflet may branch to form a trifoliate, rarely a two foliate. In addition, bracts may originate at the primary peduncle apex, growing upward alongside the secondary peduncles. Bracts also typically occur at the apex of the secondary peduncle(s), where pedicels bearing secondary and tertiary fruit originate. Pubescence on the primary peduncle grow irregularly perpendicular to the peduncle.

Stolons

Stolon production in nursery plants is good, but slightly less than that of 'Selva', and comparable to that of 'Muir'. Variety '118' will produce stolons in the fruiting field at about the same rate as 'Selva' and 'Muir' if given more than optimal chilling for maximum fruit yields.

PEST REACTIONS

Variety '118' may not be resistant to any of the known insect and disease pests common in California. It is known to be moderately susceptible to the two-spotted spider mite and to flower thrips. In high concentrations, thrips have shown to cause slight discoloration of both immature and mature fruit. It is also known to be moderately susceptible to powdery mildew and grey fruit mold. From field observations, it does not appear to be susceptible to the virus disease complexes (including 'Mild Yellow Edge') common in California. It has not been tested for susceptibility to *P. cactorium* or *C. acutatum.*

This new variety may slightly in the details above, depending upon weather, soil, location and evaluation date.

We claim:

1. A new distinct strawberry variety, as herein described and illustrated.

* * * * *

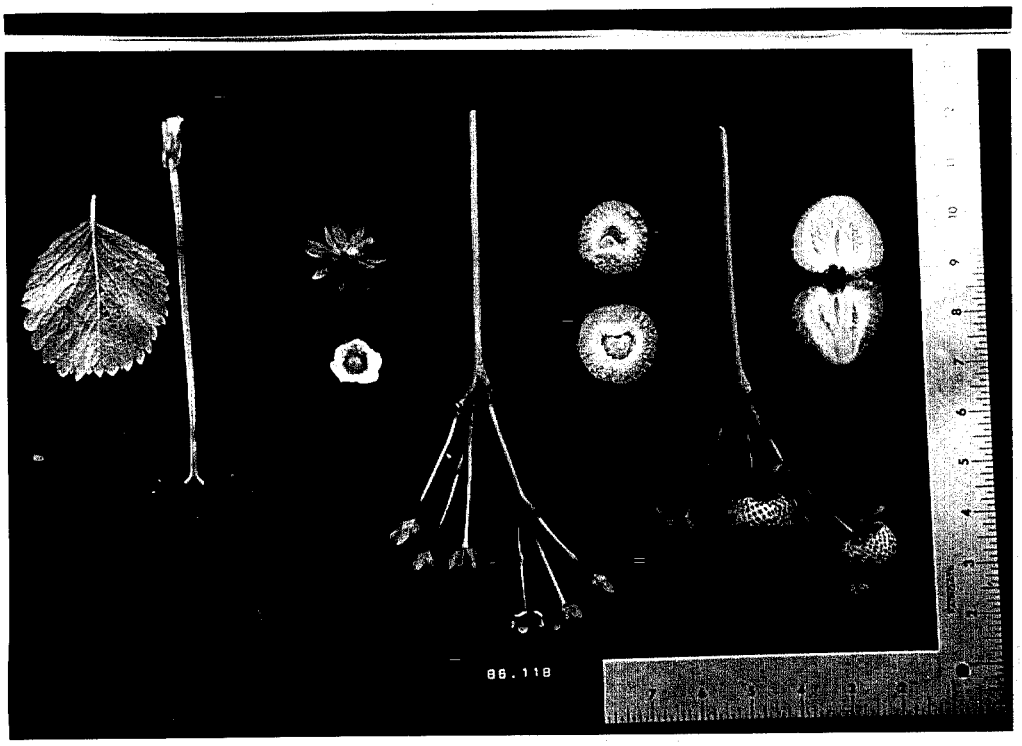
86.118

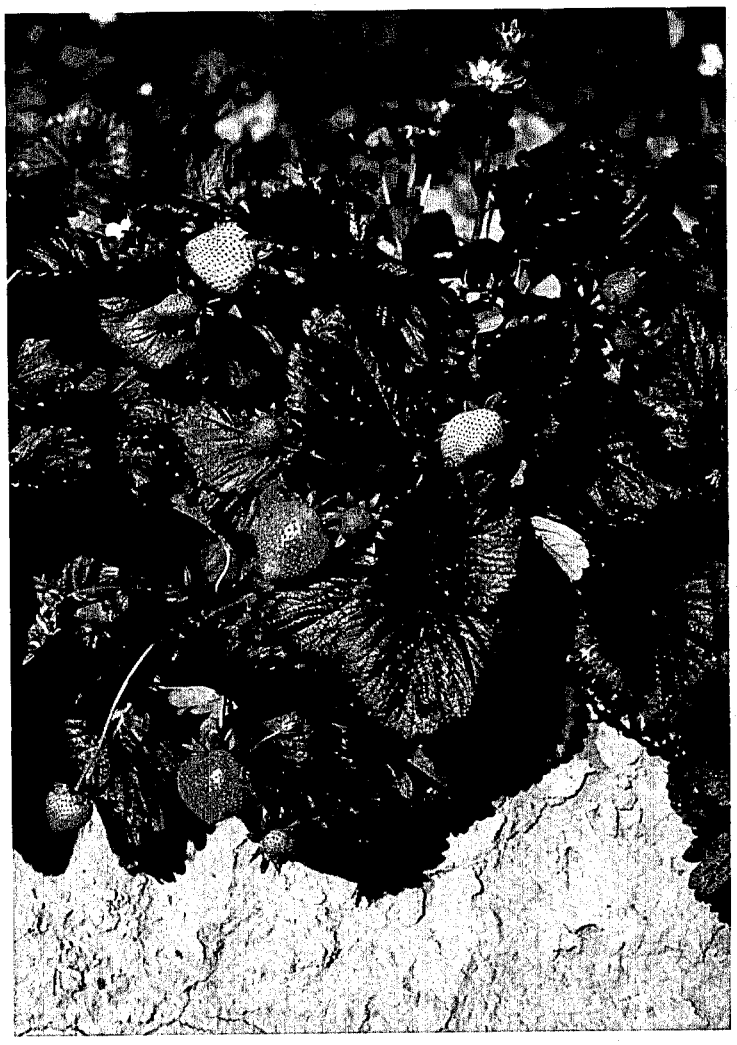

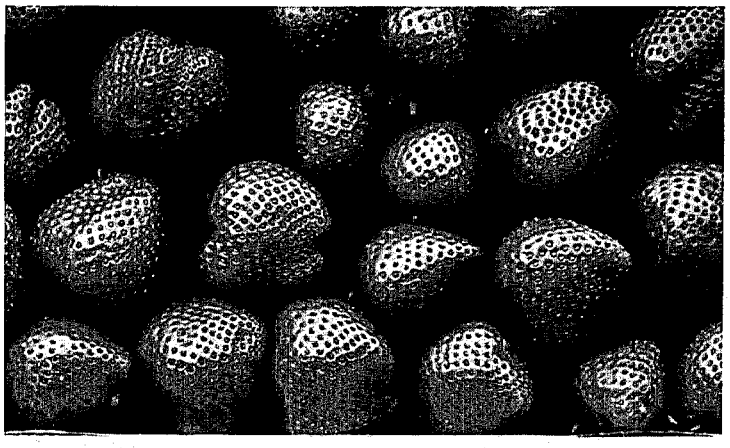
PSI 86.118
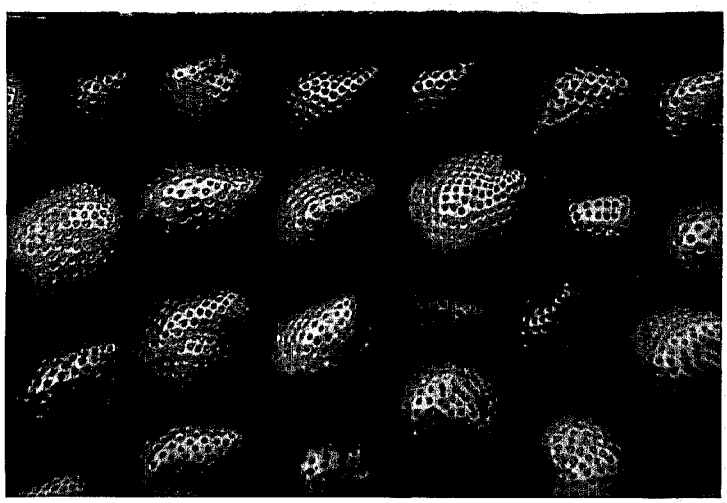

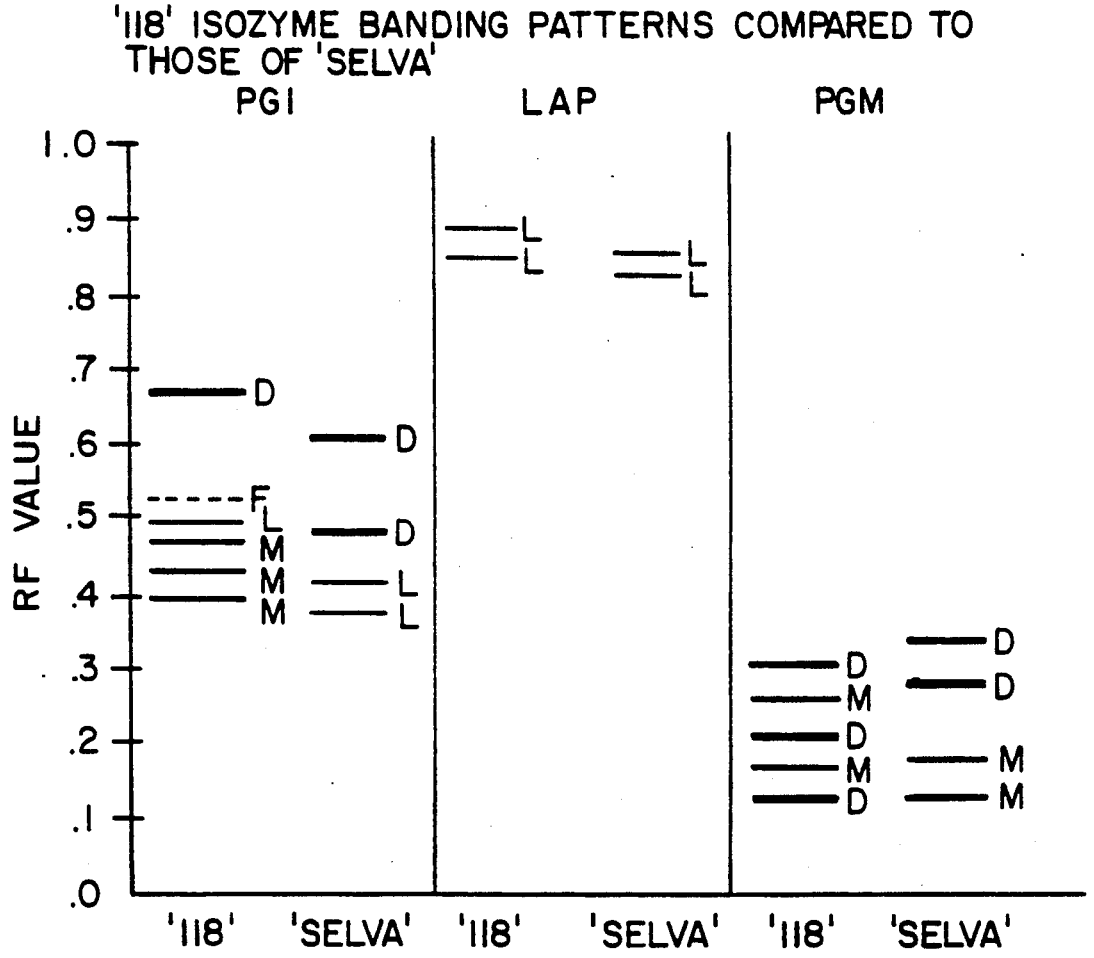
D=DARK BAND
M=MODERATELY DARK BAND
L=LIGHT BAND
F=FAINT BAND